US009267896B2

(12) United States Patent
Cha et al.

(10) Patent No.: US 9,267,896 B2
(45) Date of Patent: Feb. 23, 2016

(54) URANIUM ANALYSIS USING LUMINESCENCE ENHANCING OXIDANT AND OXIDANT COMPOSITION

(71) Applicants: KOREA ATOMIC ENERGY RESEARCH INSTITUTE, Daejeon (KR); KOREA HYDRO & NUCLEAR POWER CO., LTD., Seoul (KR)

(72) Inventors: Wan-Sik Cha, Daejeon (KR); Euo-Chang Jung, Daejeon (KR); Hye-Ryun Cho, Daejeon (KR)

(73) Assignee: KOREA ATOMIC ENERGY RESEARCH INSTITUTE, Seoul (KR)

( * ) Notice: Subject to any disclaimer, the term of this patent is extended or adjusted under 35 U.S.C. 154(b) by 664 days.

(21) Appl. No.: 13/729,986

(22) Filed: Dec. 28, 2012

(65) Prior Publication Data
US 2014/0080217 A1 Mar. 20, 2014

(30) Foreign Application Priority Data

Sep. 20, 2012 (KR) .................. 10-2012-0104615

(51) Int. Cl.
*G01N 21/76* (2006.01)
*G01N 21/64* (2006.01)
*G01N 21/00* (2006.01)

(52) U.S. Cl.
CPC .............. *G01N 21/76* (2013.01); *G01N 21/643* (2013.01); *G01N 21/6408* (2013.01)

(58) Field of Classification Search
CPC .. G01N 21/6408; G01N 21/76; G01N 21/643
USPC ................................................ 82/82; 436/82
See application file for complete search history.

(56) References Cited

U.S. PATENT DOCUMENTS 4,112,044 A * 9/1978 Miyake et al. ..................... 423/7
4,198,568 A * 4/1980 Robbins et al. ............. 250/459.1
(Continued)

FOREIGN PATENT DOCUMENTS

JP 06-049361 2/1994
KR 1020120079941 A 7/2012

OTHER PUBLICATIONS

Jung et al., "Conference of Korea Society of radioactive waste," pp. 235-236, 2007.
(Continued)

*Primary Examiner* — Rebecca M Fritchman
(74) *Attorney, Agent, or Firm* — Hauptman Ham, LLP

(57) ABSTRACT

According to the present invention, there is provided a method of determining a concentration of uranium including: a) a primary measuring step of measuring luminescence intensity or luminescence attenuation of uranium (VI) of an oxidant added sample obtained by adding an oxidant composition to a detection target sample; b) a secondary measuring step of adding different volumes of standard solution containing uranium (VI) having a predetermined concentration to a plurality of oxidant added samples, respectively, and then measuring luminescence intensity or luminescence attenuation of uranium (VI) contained in each standard solution added sample; and c) a calculating step of calculating a concentration of uranium (VI) contained in the detection target sample by a standard addition method based on the primary and secondary measurements. With the method for determining a concentration of uranium according to the present invention, the concentration of uranium may be further rapidly and accurately analyzed.

14 Claims, 3 Drawing Sheets

(56) References Cited

U.S. PATENT DOCUMENTS 4,599,512 A * 7/1986 Bushaw .................. 250/253
2013/0206599 A1 * 8/2013 Celier ..................... 205/46

OTHER PUBLICATIONS

Korean Notice of Allowance for corresponding Korean Patent Application No. 10-2012-010-4615, dated Apr. 22, 2014.

Cha et al.: "TRLFS Studies on Indirect Determination of U(IV) in Biological Samples Containing Mixed U(IV/VI) Species," Transactions of the Korean Nuclear Society Spring Meeting, Jeju, Korea, May 17-18, 2012.

Cha et al.: "TTRLFS Studies on Luminescence Enhancement of U(VI) Using Oxidants for Quencher Species in Samples," Transactions of the Korean Nuclear Society Autumn Meeting, Gyeongju, Korea, Oct. 25-26, 2012.

* cited by examiner

URANIUM ANALYSIS USING LUMINESCENCE ENHANCING OXIDANT AND OXIDANT COMPOSITION

CROSS-REFERENCE TO RELATED APPLICATIONS

This application claims priority under 35 U.S.C. §119 to Korean Patent Application No. 10-2012-0104615, filed on Sep. 20, 2012, in the Korean Intellectual Property Office, the disclosure of which is incorporated herein by reference in its entirety.

TECHNICAL FIELD

The following disclosure relates to a uranium analysis using a luminescence enhancing oxidant and an oxidant composition.

BACKGROUND

Uranium, a naturally occurring element in earth's crust, exists in soil, sediments, plants, and river water, and particularly, it is known that 0.76 µg of uranium per 1 g of soil is present in the soil. Among uranium isotopes, 238U (99.2745%) is a dominant uranium isotope. In addition, 235U and 234U are also considered as major isotopes. All of them are classified as a radioactive material emitting α-ray and having a long half-life. Use of uranium, which is an actinide element, has increased; it is used as a raw material required for manufacturing a new kind of chemical species or alloys due to its own physical/chemical properties and as nuclear fuel in nuclear power generation, or the like.

A quantitative analytical technology for uranium is essential for controlling processes related to mining, purification, processing, separation, and recovery of uranium. Particularly, analytical techniques of uranium related to environmental health have been developed extensively. For example, in order to study the effects of uranium variability in river water according to geological conditions or artificially released uranium on the ecosystem, or the like, or in order to track migration pathways of uranium in groundwater systems, developments of appropriate analytical methods have been required for measuring a concentration of a trace amount of uranium in samples. Currently, for uranium analysis, α-spectroscopy, laser luminescence spectroscopy, inductively coupled plasma (ICP)-mass spectroscopy (MS), or the like, is mainly used. Among them, a spectroscopic technique using luminescence properties of uranium is a highly sensitive and non-destructive method as compared with the alpha spectroscopy.

The laser induced luminescence spectroscopy may be divided into a continuous wave laser spectroscopy and a pulse laser spectroscopy according to the type of laser source. Use of continuous wave laser may be advantageous to obtain strong luminescent signal due to the accumulation of continuous luminescence from uranium species in a sample. A detector system may be comprised of a fiber optic light guide, a monochromator, and a photo-multiplier tube, or the like, which thereby allows a highly sensitive luminescence measurement. In the case in which luminescence properties of chemical species to be measured are well-defined under controlled sample conditions (pH, concentration, ionic strength, temperature, or the like), direct measurements of luminescence intensity are simple and advantageous ways for uranium quantification. Particularly, luminescence intensity at a wavelength range of 508 to 525 nm where a strong luminescence peak lies can be directly used for the uranium quantification. On the other hand, a measurement system using the pulse laser system may be more complicated (See below). However, attenuation waveforms of luminescent signal after each pulse can be measured separately in addition to luminescence intensity. Using such luminescence properties, i.e., lifetime and spectrum peak positions, more selective identification of each uranium species can be achieved; a luminescent signal from a single species may be measured and distinguished even though a sample contains a mixture of uranium chemical species. Such a pulse laser-based luminescence technique is typically called time-resolved laser-induced fluorescence spectroscopy (TRLFS), and a detailed description is provided below.

Uranium(VI) (oxidation number: 6+) exhibits strong emission when the pulse laser is irradiated. This luminescence (LM) emission has been used to selectively distinguish various uranium species in a sample since each chemical species has a unique luminescence spectrum and luminescence lifetime. For example, a luminescence lifetime of uranyl ions ($UO_2^{2+}$) in a strong acidic aqueous solution is about 1 to 2 µs, but luminescence lifetimes of $(UO_2)_2(OH)_2^{2+}$ and $(UO_2)_3(OH)_5^+$, which are hydrolyzed species present in weak acidic aqueous solution, are 6 to 8 µs and 10 to 15 µs, respectively, so that they can be distinguished from each other. In addition, the luminescence spectrum of each species also has different peak positions from each other, that is, a unique spectral signature of each U(VI) species. In addition, when an organic or inorganic ligand is present in aqueous solution, uranium ions form metal-ligand complexes, wherein luminescence properties of these complex species are sensitively changed according to a composition of the aqueous solution. Therefore, these luminescence properties are useful to track physicochemical behaviors of uranium ions in the aqueous solution, and a description thereof is disclosed in Korean Patent Laid-Open Publication No. 10-2012-0079941 (Patent Document 1).

In order to measure both luminescence intensity and luminescence lifetime of uranium(VI), a pulse laser (light source), a monochromator, and a detector such as a photo-multiplier tube (PMT) detector are required. Generally, a laser source having an excitation wavelength of 420 nm or less and a pulse width of several nanometers is used. Particularly, in order to measure the luminescence lifetime, devices such as an oscilloscope capable of measuring the attenuation of luminescence signals after irradiation of a laser pulse and a boxcar (a time-gate controller and signal averager) for tracking the attenuated luminescence signal at each time point are required. In TRLFS, a set of these devices is typically used to simultaneously measure luminescence intensity and luminescence attenuation as well as luminescence spectrum by controlling the width of a detection gate and delay time at a level of several microseconds (µs) or less. In the case in which each chemical species, i.e., each U(VI) species, has different luminescence spectrum and lifetime, the TRLFS is a significantly effective method in distinguishing chemical species. Generally, the TRLFS is highly useful to detect and analyze uranium chemical species in an aqueous solution, which generally have short luminescence lifetimes (several µs or less).

In the case in which phosphoric acid or a polymeric form thereof is present, uranium forms $UO_2$-phosphate complexes, wherein a luminescence lifetime of this complex species is significantly longer than that of other uranium chemical species. That is, when a laser pulse having a wavelength of 425 nm or less is irradiated under an acidic condition, generally, luminescence emission exhibits a long lifetime of 50 to 400 µs. Based on such luminescence characteristics of this complex, a kinetic phosphorescence analysis (KPA) method was developed for determination of uranium, which in fact is one type of TRLFS. This property, i.e., the extended lifetime of U(VI), contributes to an increase in the measured luminescence intensity of uranium. In the KPA method, after the irradiation of each laser pulse, the attenuation of light emitted at a wavelength of 515 to 520 nm is measured using a multichannel counter. Then, the luminescence decay profile is analyzed based on the principle that the y-intercept value obtained by extrapolating a plot of log values of the measured luminescence intensity as a function of time is in proportion to a concentration of uranium. Along with sample pre-treatment procedures performed prior to the spectroscopic measurement, the KPA method is a highly sensitive analytical method enough to have a limit of detection of several ten ng/L (<nM).

However, since the luminescence phenomenon of uranium as described above is observed only for uranium species in an oxidation state, 6+; uranium in other oxidation states, such as +4 and +3, are generally known to be non-luminescent. If uranium having a different oxidation state rather than 6+ is present in a sample, determination of the total uranium may be impossible. In addition, when other metal ions or inorganic/organic materials quenching uranium luminescence coexist in the sample, the luminescence lifetime and intensity may be significantly reduced. As shown in FIG. 1, although a sample containing uranium is mixed with the luminescence enhancing phosphate as mentioned above, the luminescence lifetime of uranium rapidly decreases as the concentration of reductive metal ions or organic/inorganic material increase. Therefore, prior to spectroscopic measurements, a sample pre-treatment process for separating or decomposing these interfering materials is required. The pre-treatment process is generally configured of a wet ashing process requiring high temperature (400 to 600° C.) and strong acid, and a dry ashing process. The object of the pre-treatment process is to convert uranium in lower oxidation states other than 6+ to uranium of +6 oxidation state through oxidation reactions and to reduce interfering materials by decomposing/evaporating the organic or inorganic materials. However, even after this pre-treatment process is performed, it is known that residual metal ions or other organic or inorganic ions can affect analysis sensitivity (See FIG. 1). Further, a series of such complicated and labor-intensive pre-treatment procedures increases uncertainty of the analysis and makes it difficult to implement a rapid uranium analysis. Therefore, the necessity for a more simple and accurate method of detecting a concentration of uranium has increased.

RELATED ART DOCUMENT

Patent Document (Patent Document 1) Korean Patent Laid-Open Publication No. 10-2012-0079941

SUMMARY

An embodiment of the present invention is directed to providing a method of determining a concentration of uranium having a simple pre-treatment process and high accuracy.

In one general aspect, there is provided a method of determining a concentration of uranium including: a) a primary measuring step of measuring luminescence intensity or luminescence attenuation of uranium (VI) of an oxidant added sample obtained by adding an oxidant composition to a detection target sample; b) a secondary measuring step of adding different volumes of standard solution containing uranium (VI) having a predetermined concentration to a plurality of oxidant added samples, respectively, and then measuring luminescence intensity or luminescence attenuation of uranium (VI) contained in each standard solution added sample; and c) a calculating step of calculating a concentration of uranium (VI) contained in the detection target sample by a standard addition method based on the primary and secondary measurements.

Other features and aspects will be apparent from the following detailed description, the drawings, and the claims.

DETAILED DESCRIPTION OF EMBODIMENTS

Figure 1:
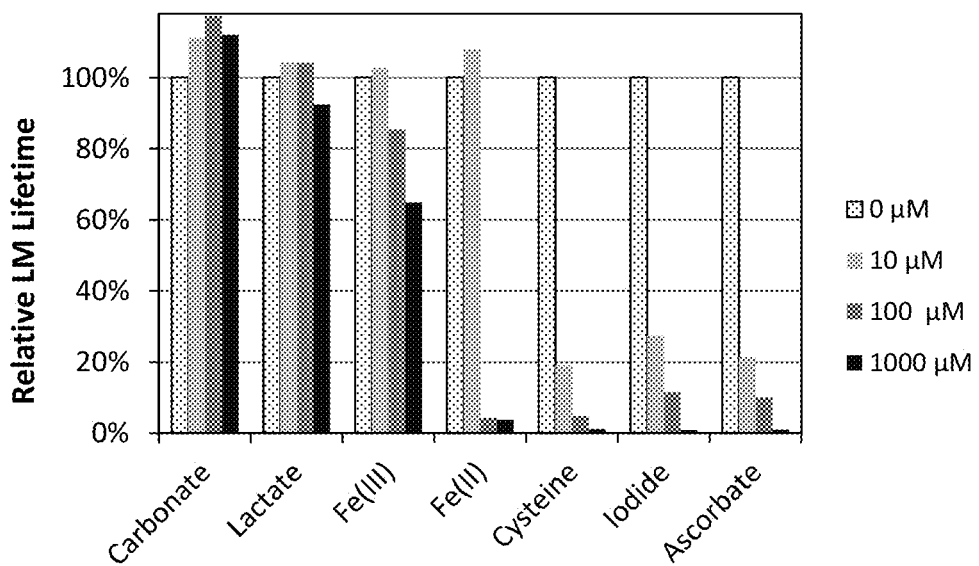
FIG. 1 is a graph showing an influence of exemplified metal ions or organic/inorganic materials on luminescence of uranium according to their concentration using a time-resolved laser-induced fluorescence spectroscopy (TRLFS).

The advantages, features and aspects of the present invention will become apparent from the following description of the embodiments with reference to the accompanying drawings, which is set forth hereinafter. The present invention may, however, be embodied in different forms and should not be construed as limited to the embodiments set forth herein. Rather, these embodiments are provided so that this disclosure will be thorough and complete, and will fully convey the scope of the present invention to those skilled in the art. The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises" and/ or "comprising," when used in this specification, specify the presence of stated features, integers, steps, operations, elements, and/or components, but do not preclude the presence or addition of one or more other features, integers, steps, operations, elements, components, and/or groups thereof. According to the present invention, "oxidant composition" and "oxidant" may be the same meaning as defined.

Hereinafter, exemplary embodiments will be described in detail with reference to the accompanying drawings.

The present invention provides a method of determining a concentration of uranium including:

a) a primary measuring step of measuring luminescence intensity or luminescence attenuation of uranium (VI) of an oxidant added sample obtained by adding an oxidant composition to a detection target sample;

b) a secondary measuring step of adding different volumes of standard solution containing uranium (VI) having a predetermined concentration to a plurality of oxidant added samples, respectively, and then measuring luminescence intensity or luminescence attenuation of uranium (VI) contained in each standard solution added sample; and c) a calculating step of calculating a concentration of uranium (VI) contained in the detection target sample by the standard addition method based on the primary and secondary measurements.

The step a) may be a step of adding the oxidant composition to the detection target sample, leaving the oxidant added sample at room temperature to 80° C. for 10 minutes to 3 hours to allow uranium (IV), metal ions, and inorganic/organic materials that are included in the detection target sample to be oxidized, and then measuring luminescence intensity or luminescence attenuation of uranium (VI).

In step a), the oxidant composition may be one or a mixture of at least two selected from hydrogen peroxide, peroxide, percarbonate, dioxide, hypochlorite, persulfate, monopersulfate, alkaline peroxide, alkaline earth metal peroxide, urea peroxide, peroxysilicate, peroxyphosphate, ozone, and organic peroxides.

The oxidant composition may be a single oxidant in a liquid state, powder type solid state, or gas state such as ozone or a mixture thereof.

In addition, the oxidant composition may be a mixture in which one or a mixture of at least two selected from hydrogen peroxide, peroxide, percarbonate, dioxide, hypochlorite, persulfate, alkaline peroxide, alkaline earth metal peroxide, urea peroxide, peroxysilicate, peroxyphosphate, and organic peroxides is mixed with on monopersulfate or ozone at a concentration ratio of 0.1 to 1.5 based on monopersulfate or ozone, monopersulfate alone, or ozone alone.

Step a) may include:

a1) oxidizing the oxidant added sample in which the oxidant composition is added to the detection target sample;

a2) preparing an oxidant-luminescence enhancer added sample A in which a luminescence enhancer is added to oxidized oxidant added sample; and a3) measuring luminescence intensity or luminescence attenuation of uranium (VI) of the oxidant-luminescence enhancer added sample A.

And, as another example, step a) may include:

a1) oxidizing an oxidant-luminescence enhancer added sample B in which a mixture of the oxidant composition and a luminescence enhancer is added to the detection target sample; and a2) measuring luminescence intensity or luminescence attenuation of uranium (VI) of the oxidant-luminescence enhancer added sample B.

A volume ratio of the oxidant to the luminescence enhancer may be 1:2 to 120.

In addition, a volume ratio of the detection target sample to the oxidant may be 1:0.01 to 0.5.

As the luminescence enhancer may include 0.01 to 0.5 mol/L of phosphate, pyrophosphate, polymeric phosphate, or a mixture thereof, and a pH thereof may be 0 to 4.

In this case, the luminescence intensity or luminescence attenuation in each step a) and step b) may be measured by laser-induced luminescence spectroscopy using a continuous wave laser or a pulse laser.

The method of using the pulse laser specifically indicates a time-resolved laser-induced fluorescence spectroscopy (TR-LFS), which is a luminescence spectroscopy including a kinetic phosphorescence analysis (KPA) method.

In the measuring of the luminescence intensity or luminescence attenuation in each step a) and step b), the luminescence intensity or luminescence attenuation may be measured at a specific wavelength, preferably, at a wavelength in a region of 508 to 525 nm among luminescence spectrum of uranium, and luminescence signals detected using a continuous wave laser may be used as a measurement value of the luminescence intensity. More preferably, the luminescence attenuation measured using the pulse laser is time-resolved, and a value obtained by integrating and averaging a signal measured in a determined attenuation time region may be used as a measurement value of the luminescence intensity.

As another method (KPA method), the luminescence attenuation in each step a) and step b) is measured, a y-intercept value calculated by expressing a log value of the luminescence intensity measured at the time of luminescence attenuation as a function of a time, and the y intercept value calculated as described above may be used as a measurement value of the luminescence intensity representing the concentration of uranium in the sample.

Step c) may be a step of calculating the measurement value of the luminescence intensity from the measured result obtained in step a) and step b) and making a calibration curve of the measurement value of the luminescence intensity of each of the standard solution added samples in which different volumes of the standard solution are added to calculate the concentration of uranium (VI) contained in the detection target sample.

In addition, the present invention may provide a method of determining a concentration further including a step of determining a concentration of uranium (IV) contained in the detection target sample using a difference between a concentration (I) of uranium (VI) determined using a detection target sample instead of the oxidant added sample of step a) and the concentration (II) of uranium (VI) determined in step c).

Hereinafter, the present invention will be described in more detail.

The present inventors studied for several years in order to solve a problem that it takes a long time in the existing method of dissolving organic/inorganic interfering materials included a detection target sample and converting uranium (IV) into uranium (VI) through a wet ashing process requiring high temperature and strong acid and a dry ashing process as a pre-treatment process for detecting a concentration of uranium. As a result, the present inventor discovered that an effect larger than that of the above pre-treatment method may be obtained in a short time by adding an oxidant instead of the above method, thereby completing the present invention.

More specifically, the present invention provides a method of determining a concentration of uranium including:

a) a primary measuring step of measuring luminescence intensity or luminescence attenuation of uranium (VI) of an oxidant added sample obtained by adding an oxidant composition to a detection target sample;

b) a secondary measuring step of adding different volumes of standard solution containing uranium (VI) having a predetermined concentration to a plurality of oxidant added samples, respectively, and then measuring luminescence intensity or luminescence attenuation of uranium (VI) contained in each standard solution added sample; and c) a calculating step of calculating a concentration of uranium (VI) contained in the detection target sample by the standard addition method based on the primary and secondary measurements.

A detailed description of each step of the method of determining a concentration of uranium according to the present invention will be provided.

First, step a) is a step of measuring luminescence intensity or luminescence attenuation of uranium (VI) of an oxidant added sample obtained by adding an oxidant composition to a detection target sample, and in step a), since the measurement is performed after uranium (IV) the metal ions, the inorganic materials, and the organic materials that are present in the detection target sample are oxidized instead of the pre-treatment process required the existing method of detecting uranium, uranium (IV) is converted into uranium (VI), and the metal ions, the inorganic materials, and the organic materials are oxidized, thereby making it possible to accurately detect the concentration of uranium.

The detection target sample according to the present invention is not limited as long as a material includes uranium ions. For example, the detecting target sample includes environmental samples, medical samples, or biological samples in which a large amount (several ten micro moles or more) of interference ions reducing luminescence efficiency of uranium or organic materials are included as well as samples extracted at a mining area, waste artificial radioactive materials such as pharmaceutical samples, weapons, or nuclear fuels, or the like. According to the present invention, a concentration of uranium included in various detecting target samples may be determined.

Figure 2:
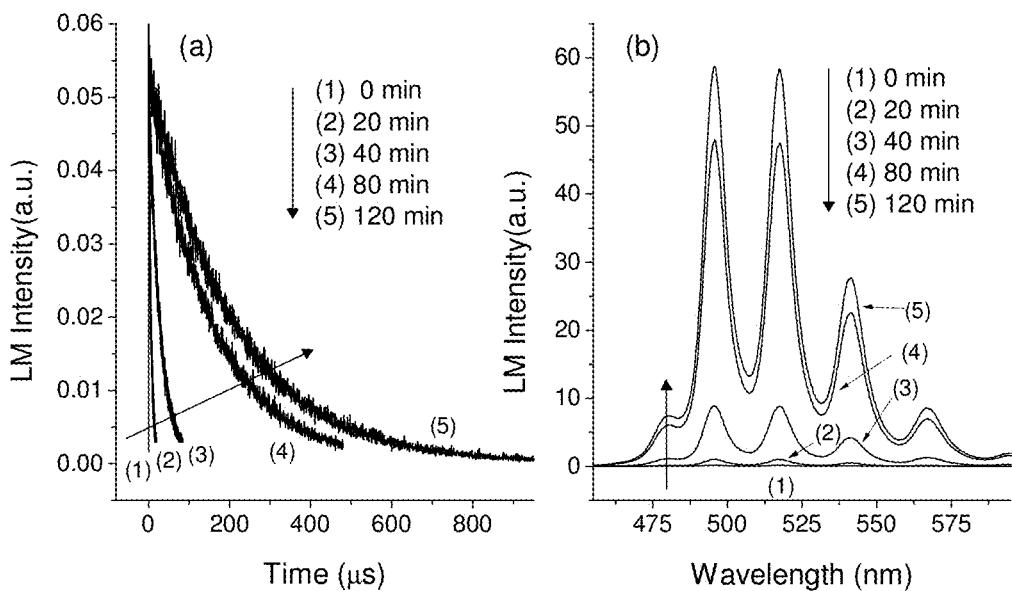
FIG. 2 is a graph showing a change in a luminescence lifetime and spectrum of uranium when monopersulfate oxidant is added to a sample including uranium and ascorbate (1 mM), which is one of reductive interfering materials.

The oxidant according to the present invention relatively rapidly reacts with reductive inorganic ions and organic materials that are present in the sample according to the composition, thereby increasing the observed luminescence lifetime and luminescence intensity (See FIG. 2). The reason is that the reductive inference materials are oxidized during the reaction time to be converted into compounds interfering less with luminescence of uranium. Therefore, as the reaction proceeds over time, the luminescence lifetime of uranium becomes longer and the luminescence intensity also subsequently increases (See FIG. 2).

Figure 3:
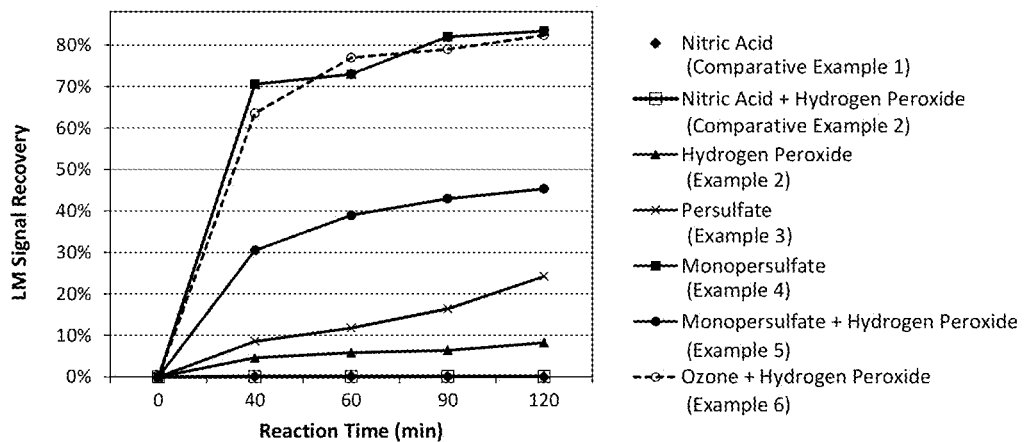
FIG. 3 is a graph showing a change in luminescence intensity over time in the case in which several oxidizing compositions are added to a sample including a mixture of interfering materials (cysteine and Fe (II)) and uranium, and oxidation is conducted at room temperature.
Figure 4:
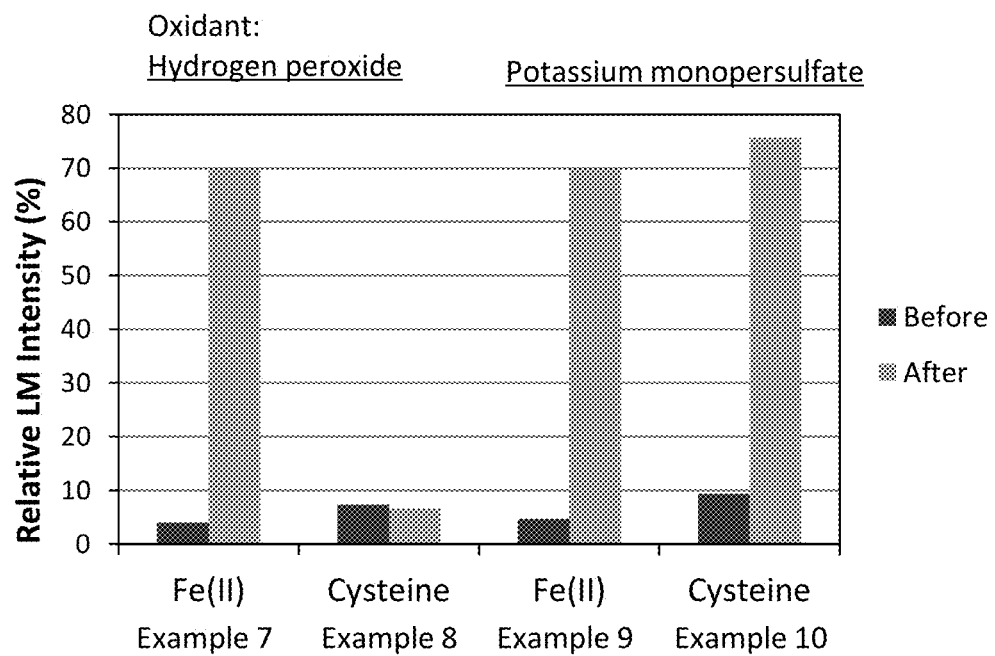
FIG. 4 is a graph showing the results of oxidation reaction of hydrogen peroxide and monopersulfate. Each of the oxidants was added to the sample including cysteine or Fe (II), which is the interfering material, and luminescence intensities of uranium before and after oxidation reaction for 2 hours at room temperature were compared.

The oxidant composition requires a predetermined reaction time in order to oxidize the interfering material after being added to the detection target sample and mixed with the sample. According to the present invention, after the oxidant composition is added to the detection target sample and then left at room temperature for 10 minutes to 3 hours to allow uranium (IV), the metal ions, and the inorganic/organic materials that are included in the detection target sample to be oxidized, the luminescence intensity or luminescence attenuation of uranium (VI) may be measured. A rate of the oxidation reaction by the oxidant may be different according to the kinds of oxidants (see FIG. 3), and a kind of interfering materials may be different according to the kinds of oxidants (see FIG. 4). In addition, even in the case of using the same oxidant, the rate of the oxidation reaction may be different according to the kind of interfering materials included in the sample (See FIG. 5). Therefore, it may be preferable to use different oxidants and different compositions of the oxidant according to the kind of interfering materials included in the sample. Generally, since the oxidation reaction of the oxidant may rapidly occur at a high temperature, in the case in which a reaction temperature is maintained to be higher than room temperature, the oxidation reaction time may be reduced (See Examples in Table A). Therefore, preferably, after the oxidant is added to the detection target sample, the oxidant added sample may be left at room temperature to 100° C., more preferably, at room temperature to 80° C., for 10 minutes to 3 hours, more preferably 10 minutes to 2 hours.

In step a), in the case in which an amount of oxidized interfering materials is large after oxidation reaction, precipitation may occur. Therefore, step a) may include removing precipitates generated after oxidation reaction. After oxidation reaction, the precipitates generated in the sample solution including the oxidant may be removed by a centrifugation method or a filtering method. Further, in step a), in the case in which an excessive amount of gaseous oxidant such as ozone is present after the oxidation reaction, a purging process of adding air or other inert gas (argon, nitrogen) to remove the gaseous oxidant may be included.

With the oxidant according to the present invention, the existing long pre-treatment process such as a wet ashing process requiring high temperature and strong acid, a dry ashing process, or the like, for detecting a concentration of uranium may be substituted. That is, in the case of substituting the method according to the present invention for the existing sample pre-treatment process that is complicated and takes an average of 2 days or more or using the method according to the present invention together with the existing method, the pre-treatment process may be simplified, and an overall sample preparation time may be reduced.

The oxidant composition may contain one or at least two selected from hydrogen peroxide ($H_2O_2$), peroxide ($O_2^{2-}$), peroxycarbonate ($CO_4^{2-}$), dioxide, ($O^{2-}$), hypochlorite ($ClO^-$), persulfate ($S_2O_8^{2-}$), monopersulfate ($SO_5^{2-}$), alkaline peroxide, alkaline earth metal peroxide, urea peroxide, peroxysilicate, peroxydiphosphate, peroxypyrophosphate or peroxytripolyphosphate, ozone ($O_3$), and organic peroxides.

As an example of alkaline peroxide and alkaline earth metal peroxide, there is lithium, sodium, potassium, calcium, zinc, or magnesium peroxide, or the like.

Another example of peroxides except for hydrogen peroxide, there are organic peroxides such as dialkyl peroxide, diacylperoxide, performed percarboxylic acid, or the like, inorganic peroxides, hydroperoxide, or the like. A specific example of organic peroxide and hydroperoxide includes diacryl and dialkyl peroxide such as dibenzoyl peroxide, t-butyl hydroperoxide, dilauryl peroxide, dicumyl peroxide, and a mixture thereof.

The most preferable example of the oxidant composition according to the present invention may include monopersulfate or ozone. Monopersulfate and ozone rapidly oxidize reductive organic compounds such as ascorbate and cysteine to increase the luminescence lifetime and luminescence intensity of uranium (VI) observed at the time of measuring time-resolved luminescence signals. A change in the luminescence lifetime and luminescence intensity before and after injection of monopersulfate is shown in FIG. 2. A kind of monopersulfate according to the present invention is not particularly limited, but may be potassium monopersulfate, or the like.

All of the oxidant compositions described above are water-soluble and may be prepared as an aqueous stock solution containing the oxidant composition, but is not limited. A physical states and forms of the oxidant composition and a reaction method with samples may be different according to the kind of oxidants.

As needed, an aqueous diluent solvent including one containing electrolytes may be used. A large amount of electrolytes such as 0.05 to 0.5 M (mol/L) of sodium perchlorate ($NaClO_4$) or potassium sulfate ($K_2SO_4$) is added to the diluent solvent, such that ionic strength may be fixed.

The oxidant composition may be a single oxidant in a liquid state, a granule or powder type solid state, or a gas state such as ozone or a mixture thereof. In the case of the solid, the oxidation reaction in step a) may be performed by directly injecting the solid oxidant composition into aqueous sample aqueous solution. In the case of gas such as ozone, an aqueous solution saturated with oxidant gas generated in an oxidant gas generator such as an ozonizer may be used as a stock solution of the oxidant. As another method, a method of continuously bubbling oxidant gas in the sample solution during the oxidation reaction may be used. In this case, a concentration of the gas oxidant may be changed by adjusting an amount of gas passing through the sample per unit time (for example, g/h).

In addition, in the case in which a large amount of oxidant remains after the oxidation reaction, since the luminescence intensity of uranium may be reduced, the lower the concentration of the oxidant in the oxidant added sample in step a) is, the more preferable it is. More specifically, in step a), a concentration of all the oxidants included in the oxidant added sample may be 0.1 to 200 mM.

More preferably, the oxidant composition may be a mixture in which one or a mixture of at least two selected from hydrogen peroxide, peroxide, percarbonate, dioxide, hypochlorite, persulfate, alkaline peroxide, alkaline earth metal peroxide, urea peroxide, peroxysilicate, peroxyphosphate, and organic peroxides is mixed with on monopersulfate or ozone at a concentration ratio of 0.1 to 1.5 based on monopersulfate or ozone, monopersulfate alone, or ozone alone.

In the above range of the concentration ratio, the oxidation reaction may be promoted. The oxidant may be added so that a volume ratio of the oxidant to the detecting target sample is 0.01 to 0.5:1, and in the above range, the oxidation may be effectively conducted at room temperature.

In step a), the oxidant composition may include one or at least two selected from hydrogen peroxide, peroxide, percarbonate, dioxide, hypochlorite, persulfate, monopersulfate, alkaline peroxide, alkaline earth metal peroxide, urea peroxide, peroxysilicate, peroxyphosphate, ozone, and organic peroxides. A stock solution of the oxidant composition containing a mixture of the selected oxidant may have a concentration of 0.2 to 15(w/w) %.

In this case, in step a), the luminescence enhancer may be added, and more specifically, step a) may include:

a1) oxidizing the oxidant added sample in which the oxidant is added to the detection target sample;

a2) preparing an oxidant-luminescence enhancer added sample A in which a luminescence enhancer is added to oxidized oxidant added sample; and a3) measuring luminescence intensity or luminescence attenuation of uranium (VI) of the oxidant-luminescence enhancer added sample A, and, as another example, step a) may include:

a1) oxidizing an oxidant-luminescence enhancer added sample B in which a mixture of the oxidant composition and a luminescence enhancer is added to the detection target sample; and a2) measuring luminescence intensity or luminescence attenuation of uranium (VI) of the oxidant-luminescence enhancer added sample B.

The luminescence enhancer means a solution mixed with the sample in order to form the phosphate complex and may include 0.01 to 0.5M (mol/L) of phosphate, pyrophosphate, polymeric phosphate, or a mixture thereof. In addition, the luminescence enhancer may have pH of 0 to 4. As a commercial solution that may be used as the luminescence enhancer, Uraplex®, or the like, may be preferable.

The detection target sample, the oxidant, and the luminescence enhancer according to the present invention may be formed at an appropriate ratio, wherein a volume ratio of the oxidant to luminescence enhancer may be 1:2 to 120. Generally, since luminescence of uranium is measured under the condition that a volume ratio of the sample to luminescence enhancer is 1:1 to 1:1.5, when the volume ratio of the luminescence to the oxidant is less than 2, the concentration of uranium in the sample may be reduced due to dilution effects, and the volume ratio is more than 120, highly concentrated stock solution of the oxidant is required, such that there are solubility problems in preparation of the oxidant.

In addition, a volume ratio of the detection target sample to the oxidant may be 1:0.01 to 0.5. When the volume ratio of the oxidant is less than 0.01, highly concentrated stock solution of the oxidant is required, such that there are problems in preparing the oxidant and solubility, and when the volume ratio is more than 0.5, the dilution effect may occur.

The luminescence may not be added to the sample in some cases. For example, in the case in which the degree of oxidation of the sample and distribution of uranium chemical species in the oxidized sample after the oxidation reaction are constantly maintained and thus continuous wave laser spectroscopy is used, the luminescence intensity and luminescence attenuation of uranium may be measured in the sample in which only oxidant is added as in the case of an oxidant added sample C.

Next, step b) will be described in detail.

Step b) is a step of adding different volumes of standard solution containing uranium (VI) having a predetermined concentration to a plurality of oxidant added samples, respectively, and then measuring luminescence intensity or luminescence attenuation of uranium (VI) contained in each standard solution added sample.

More specifically, the plurality of oxidant added samples having the same volume in step a) are prepared, and different volumes, for example, sequential volumes such as 10 ml, 20 ml, 30 ml, and the like, of the standard solution including uranium (VI) at a predetermined concentration are added to the plurality of oxidant added sample, respectively, thereby preparing standard solution added samples. Luminance intensities and luminance attenuation of uranium (VI) in each of the standard solution added samples are measured, which is performed in step b).

The standard solution means a solution in which the detection target material, that is, uranium (VI) and other materials are contained at a randomly predetermined concentration, wherein kinds and contents of materials needs to be accurately expressed. The standard solution according to the present invention may satisfy the following conditions.

i) 0.1 to 10 mM of uranium (VI)
ii) 0.05 to 0.5M of sodium perchlorate ($NaClO_4$), and
iii) pH of standard solution: 0 to 4

Next, step c) will be described in detail.

Step c) is a step of calculating a concentration of uranium (VI) contained in the detection target sample based on the primary and secondary measurements.

More specifically, after measuring the luminescence attenuation of uranium (VI) in the oxidant added sample in the primary measurement and measuring the luminescence intensity or luminescence attenuation of uranium (VI) in the standard solution added sample according to each volume of the added standard solution in the secondary measurement, the concentration of uranium (VI) contained in the detection target sample is calculated based on the primary and secondary measurements in step c). Generally, a method of calculating a concentration of a target ingredient in a sample using step a) to c) is called a standard addition method.

More specifically, the luminescence intensity and luminescence attenuation in steps a) and b) according to the present invention may be measured by laser-induced spectroscopy using a continuous wave laser or pulse laser. In the laser-induced spectroscopy, a laser having a wavelength of 420 nm or less is generally used as a light source. In the case of using the continuous wave laser, a value obtained by integrating luminescence intensities measured in the overall region of the luminescence spectrum of the laser irradiated uranium chemical species may be used, a value obtained by integrating signals at a predetermined wavelength region (508 to 525 nm) corresponding to a spectrum peak at which the maximum luminescence signal appears may be used, or a method of selecting a wavelength at which the maximum luminescence signal appears among spectrum peaks at which a large luminescence signal appears to measure an emitted signal may be used.

More preferably, the luminescence intensity and luminescence attenuation in steps a) and b) according to the present invention may be measured by the time-resolved laser-induced fluorescence spectroscopy (TRLFS). As described in the background, the luminescence attenuation and luminescence spectrum (or luminescence intensity) as shown in FIG. 2 may be obtained using a detection system configured of a pulse laser, a spectrometer, photo-multiplier tube (PMT) detector, an oscilloscope, a boxcar, and a computer for analyzing signals. Therefore, data on the luminescence intensity and luminescence attenuation in each sample required for quantitative analysis in step c) may be obtained. For example, the luminescence attenuation measured after irradiation of the pulse laser can be time-resolved, and a value obtained by integrating and averaging a signal measured in a determined attenuation time period may be used as a measurement value of the luminescence intensity.

In addition, according to the present invention, the luminescence intensity or luminescence attenuation in each step a) and step b) may be measured by the kinetic phosphorescence analysis (KPA) method. In the KPA method, which is one kind of TRLFS, after irradiation of the laser pulse, attenuation of light emitted at a wavelength of 515 to 520 nm is measured using multi-channel counter, the KPA method uses the principle that a y-intercept value obtained by extrapolating a log value of the measured luminescence intensity as a function of a time is in proportion to a concentration of uranium. Here, the calculated y-intercept value is used as a measurement value of the luminescence intensity that represents the concentration of uranium in the sample. Generally, measurement value of the luminescence intensity may be calculated simultaneously with measurement of the luminescence of uranium using a commercial KPA device.

That is, in the present invention, the measurement value may be obtained by the primary and secondary measurements performed under the same conditions (pH, temperature, ionic strength, and the like) with one method selected from the above-mentioned laser spectroscopy, and a calibration curve of the measurement value of the luminescence intensity of each of the standard solution added samples in which different volumes of the standard solution are added is made, such that the concentration of uranium (VI) contained in the detection target sample may be calculated.

Figure 5:
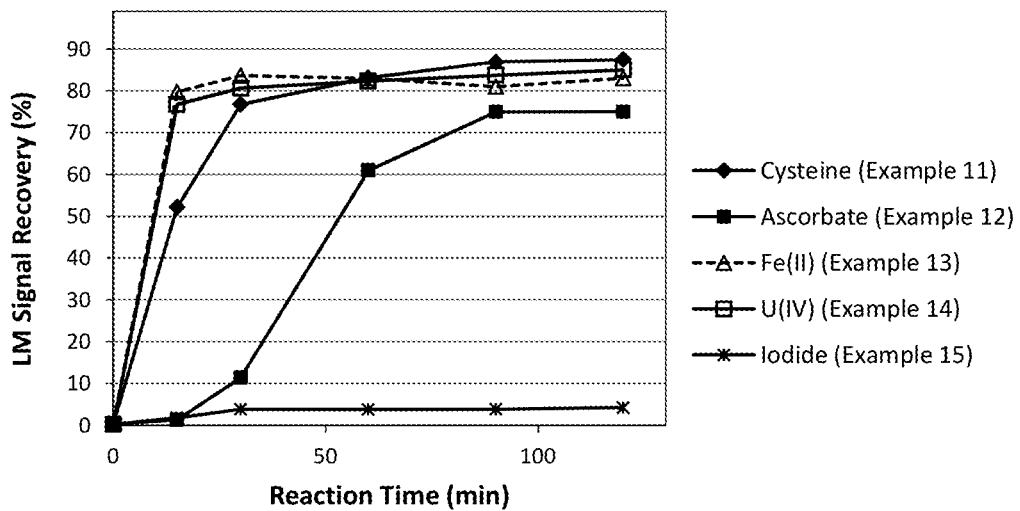
FIG. 5 is a graph showing a change in luminescence intensity of uranium over time in a reaction process at room temperature when the monopersulfate oxidant is added to a sample including the selected interfering material and uranium.

According to the present invention, a concentration of uranium of other valence states that +6, such as a concentration of uranium (IV) included in the detection target sample containing uranium (VI) as well may be calculated. As shown in FIG. 5, uranium (IV) included in the sample may be oxidized to uranium (VI) using the oxidant according to the present invention. In present invention, the method of determining uranium of other valence states than uranium (VI) using properties of the oxidant as describe above will be suggested.

More specifically, the method according to the present invention further includes a step of determining a concentration of uranium (IV) contained in the detection target sample using a difference between a concentration (I) of uranium (VI) determined using a detection target sample without oxidant instead of the oxidant added sample of step a) and the concentration (II) of uranium (VI) determined in step c).

More specifically, the method of determining a concentration of uranium includes:

a) a primary measuring step of measuring luminescence intensity or luminescence attenuation of uranium (VI) of an oxidant added sample obtained by adding a luminescence enhancer and the oxidant to a detection target sample;

b) a secondary measuring step of adding different volumes of standard solution containing uranium (VI) having a predetermined concentration to a plurality of oxidant added samples and then measuring luminescence intensity or luminescence attenuation of uranium (VI) contained in each standard solution added sample;

c) a step of calculating the concentration (II) of the uranium (VI) contained in the detection target sample based on the primary and secondary measurements;

d) a tertiary measuring step of measuring the luminescence intensity or luminescence attenuation of uranium (VI) in the luminescence enhancer added detection target sample without oxidant added;

e) a quaternary measuring step of adding different volumes of standard solution containing uranium (VI) having a predetermined concentration to a plurality of detection target samples in step d) and then measuring luminescence intensity or luminescence attenuation of uranium (VI) contained in each standard solution added sample;

f) a step of calculating the concentration (I) of the uranium (VI) contained in the detection target sample based on the tertiary and quaternary measurements; and g) a step of calculating a concentration of uranium (IV) contained in the detection target sample using a difference between the concentration (I) of uranium (VI)) in step f) and the concentration (II) of uranium (VI) determined in step c).

Figure 6:
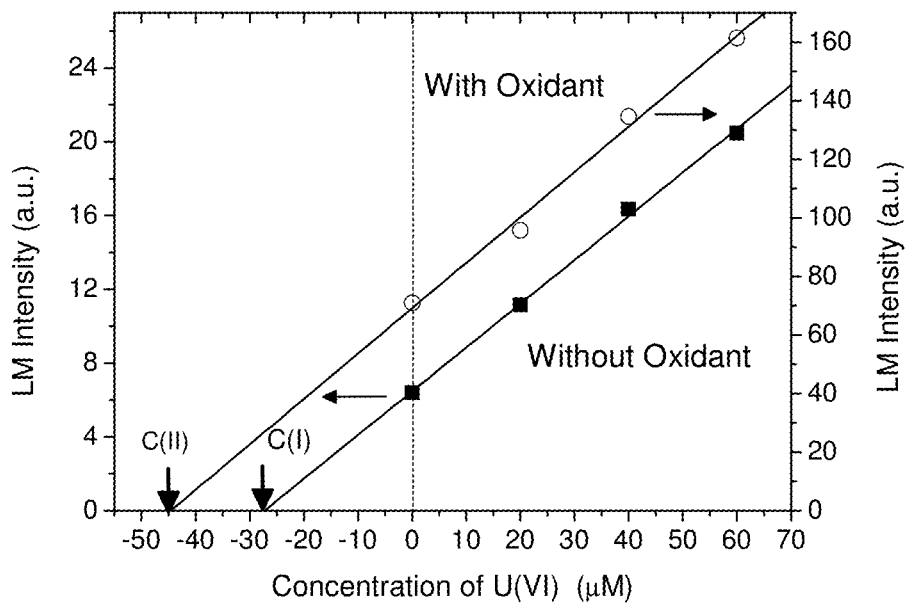
FIG. 6 is a graph showing a standard addition method by measuring luminescence of uranium in a microorganism culture media sample including both of uranium (IV) and uranium (VI) to determine concentrations of uranium (IV) and uranium (VI). The Luminescence intensities of uranium before and after oxidation reaction were measured by a time-resolved fluorescence spectroscopy using monopersulfate as an oxidant. Concentrations of uranium (VI) in the sample before and after the oxidation reaction were determined through linear extrapolation by the standard addition method, and the results were shown as C(I) and C(II), respectively.

As shown in FIG. 6, according to the method as described above, in the case in which uranium of the detection target sample is comprised of a mixture of uranium (IV) and uranium (VI), the concentration (II) of uranium (VI) is calculated based on the primary and secondary measurements, the concentration (I) of uranium (VI) of the detection target sample in which the oxidant is not added, and then the concentration of uranium (IV) contained in the detection target sample may be calculated using the difference. As shown in FIG. 6, results in each of the steps may be shown, and the concentration of uranium (VI) in the sample mixture before and after adding the oxidant may be calculated by the standard addition method. As a result, both of the concentrations of uranium (IV) and uranium (VI) may be obtained, and thus the determination of uranium having various valence states may be performed through the above method.

Next, exemplary Examples according to the present invention will be provided, but the following Examples are to illustrate the present invention, and the scope of the present invention is not limited thereto.

Example 1

An oxidant composition (a stock solution of monopersulfate) was added to a test sample including ascorbate (1 mM), which is one of the interfering organic interfering materials reducing luminescence of uranium and having a uranium concentration of 30 μM. Changes in luminescence attenuation and luminescence spectrum of uranium were monitored over time. The stock solution of monopersulfate in which $NaClO_4$ (0.1 M) and monopersulfate of Example 1 of Table 1 were dissolved in water was prepared and mixed with a sample at the volume ratio shown in Table 1. A luminescence enhancer (phosphate (0.4 M), pyrophosphate (50 mM), pH: 2) was added to the sample at a volume ratio of 1:1.5. The luminescence of uranium was measured by a time-resolved laser-induced fluorescence spectroscopy (TRLFS) using a laser having a pulse width of several ns and a wavelength of 355 nm. The luminescence attenuation was measured at a wavelength of 522 nm with a spectrometer using a PMT applied with a voltage (−800V) and collecting data using an oscilloscope connected thereto. The luminescence spectrum was measured using a spectrometer-intensified charge coupled device (ICCD) detector system that is configured separately from the system above for the attenuation measurement. Signals were collected within a luminescence attenuation section of 4 to 500 μs after each laser pulse and accumulated for 200 times pulse to produce one spectrum.

Example 2

In order to examine oxidation reaction characteristics and a reaction rate according to the kind of oxidants, after injection of the oxidants, luminescence of uranium was measured at each time point. A stock solution of hydrogen peroxide, which is an oxidant composition, was added to a test sample (concentration of uranium: 30 μM) in which Fe (II) (1 mM) and cysteine (1 mM), which are interfering materials, were contained, and then changes in luminance intensity was monitored over time. The stock solution of hydrogen peroxide in which $NaClO_4$ (0.1 M) and hydrogen peroxide of Examples of Table 1 were dissolved in water was prepared and mixed with a sample at the volume ratio shown in Table 1. A luminescence enhancer (phosphate (0.4 M), pyrophosphate (50 mM), pH: 2) was added to the sample at a volume ratio of 1:1.5. First, the luminescence spectrum was measured by the method in Example 1, and then a value obtained by integrating signals within the whole wavelength range was considered as the luminescence intensity. The measured luminescence intensity was expressed as a %-ratio compared with the luminescence intensity measured in the uranium solution without interfering materials under the same conditions to thereby be represented as a luminescence (LM) signal recovery (%) in FIG. 3.

TABLE 1

Composition of oxidants of Examples 1 to 6 and Comparative Examples 1 and 2

Concentration of oxidants in stock solution of oxidant composition (w/w %) (Volume ratio of oxidant composition mixed with detection target sample)

| Oxidant | Nitric acid | Hydrogen peroxide | Persulfate | monopersulfate | ozone |
|---|---|---|---|---|---|
| Example 2 | — | 0.9 (0.07) | — | — | — |
| Example 3 | — | — | 13 (0.04) | — | — |
| Examples 1 and 4 | — | — | — | 15 (0.04) | — |
| Example 5 | — | 0.2 (0.07) | — | 15 (0.04) | — |
| Example 6 | — | 0.2 (0.07) | — | — | 1.4 (0.07) |
| Comparative Example 1 | 15 (0.4) | — | — | — | — |
| Comparative Example 2 | 15 (0.4) | 2.0 (0.07) | — | — | — |

Examples 3 to 6

After oxidants were injected into the detection sample of Example 2 using the oxidant compositions of Examples of Table 1, the luminescence (LM) signal recovery (%) was measured by the method in Example 2. The luminescence (LM) signal recovery (%) according to each oxidant was shown in FIG. 3.

Comparative Examples 1 and 2

After oxidants were injected into the detection sample of Example 2 using the oxidant compositions in Comparative Examples of Table 1, the luminescence (LM) signal recovery (%) was measured by the method in Example 2. The luminescence (LM) signal recovery (%) according to each oxidant was shown in FIG. 3.

Examples 7 and 8

Oxidation reaction characteristics of hydrogen peroxide oxidant were compared according to the inference materials. Each oxidant was added to a test sample (concentration of uranium: 30 μM) including Fe (II) (1 mM, Example 7) or cysteine (1 mM, Example 8), which is an interfering material, and then the luminescence intensities of uranium before and after reaction for 2 hours were measured by a time-resolved laser-induced fluorescence spectroscopy (TRLFS) The stock solution of hydrogen peroxide in which $NaClO_4$ (0.1 M) and hydrogen peroxide corresponding to Examples of Table 2 were dissolved in water was prepared and mixed with a sample at the volume ratio shown in Table 1. Addition of the luminescence enhancer and measurement of the fluorescence intensity was performed by the same method as in Example 2. The measured luminescence intensity was compared with the luminescence intensity measured in the uranium solution without interfering materials under the same conditions to thereby be represented as relative LM intensity (%) in FIG. 4.

TABLE 2

Composition of oxidants of Examples 7 to 10

| Oxidant | Concentration of oxidants in stock solution of oxidant composition (w/w %) (Volume ratio of oxidant composition mixed with detection target sample) | |
|---|---|---|
| | Hydrogen peroxide | monopersulfate |
| Examples 7 and 8 | 0.5 (0.07) | — |
| Examples 9 and 10 | — | 8.0 (0.04) |

Examples 9 and 10

Monopersulfate oxidant was added to a test sample including Fe (II) (1 mM, Example 9) or cysteine (1 mM, Example 10), which is an interfering material, and then oxidation reaction characteristics thereof were compared. The relative LM intensities before and after injection of the oxidant were measured by the method in Examples 7 and 8 using the oxidant compositions of Examples of Table 2. The relative luminescence intensities were shown in FIG. 4.

Examples 11 to 15

In order to measure oxidation reaction characteristics and a reaction rate of interfering materials with respect to monopersulfate oxidant, after injection of the oxidants, luminescence of uranium was monitored over time. 10 wt % of a stock solution of monopersulfate obtained by dissolving monopersulfate in water was mixed with a test sample (concentration of uranium: 30 μM) including interfering materials in Table 3 at a volume ratio of 0.05. After addition of the oxidant, the changes in luminescence intensity of uranium were measured by the same method as in Example 2 at each time point. A luminescence enhancer was added to the sample by the same method as in Example 2, and then LM signal recovery was measured. The measured LM signal recovery (%) was shown in FIG. 5.

TABLE 3

Concentration of interfering materials in samples of Example 11 to 15

Concentration of interfering material (mmol/L)

| | Cysteine | Ascorbate | Fe (II) | Uranium (IV) | Iodine ions |
|---|---|---|---|---|---|
| Example 11 | 2.2 | — | — | — | — |
| Example 12 | — | 2.1 | — | — | — |
| Example 13 | — | — | 2.8 | — | — |
| Example 14 | — | — | — | 0.03 | — |
| Example 15 | — | — | — | — | 1.1 |

Examples 16 to 19

In order to measure an influence of a temperature on the reaction between monopersulfate (MPS) oxidant and interfering materials, luminescence of uranium was monitored over time. 17 wt % of a stock solution of monopersulfate, which is an oxidant composition, was mixed with a test sample (concentration of uranium: 30 μM) including interfering materials in Table 4 at a volume ratio of 0.04. After addition of the oxidant at different temperatures, that is, at room temperature (25° C.), 45° C., and 65° C., the changes in luminescence intensity of uranium was monitored over time by the same method as in Example 2. A luminescence enhancer was added to the sample by the same method as in Example 2. Based on a value obtained by measuring luminescence intensity of a sample without inference materials at each temperature, a luminescence of the sample including the interfering material was measured, thereby calculating a LM signal recovery (%). Time required until that the LM signal recovery is more than 70% was shown in Table A.

TABLE A

| Oxidant | Reagent[1] | Temperature | | |
|---|---|---|---|---|
| | | 25° C. | 45° C. | 65° C. |
| MPS | A(Example 16) | <10[2] | <10 | <10 |
| | B(Example 17) | <10 | <10 | <10 |
| | C(Example 18) | 60 | 15 | 12 |
| | D(Example 19) | 89 | 83 | 62 |
| APS | B(Example 20) | <10 | 18 | 21 |
| | C(Example 21) | Slow[3] | slow | 370 |
| | D(Example 22) | Slow | slow | 125 |
| | E(Example 23) | Slow | — | 75 |

[1]Reagent A, B, C and U(IV), Fe(II), cysteine and ascorbic acid, respectively; Reagent E is a mixture of Fe(II) and cysteine of 1 mM each.
[2]Time (min) required for oxidation to achieve 70% recovery of LM intensity (see details in the text)
[3]Slow oxidation observed exhibiting less than 2% LM recovery in 3 h.

TABLE 4

Composition of oxidants of Examples 16 to 23

Concentration of interfering materials (mmol/L)

| | Uranium (IV) | Fe (II) | Cysteine | Ascorbate |
|---|---|---|---|---|
| Example 16 | 0.04 | — | — | — |
| Examples 17 and 20 | — | 2.0 | — | — |
| Examples 18 and 21 | — | — | 2.0 | — |
| Examples 19 and 22 | — | — | — | 2.0 |
| Example 23 | — | — | 1.0 | 1.0 |

Examples 20 to 23

An influence of a temperature on the oxidation reaction of interfering materials in Table 4 was measured using an oxidant (persulfate) (APS) in detection samples of Examples 16 to 19. The luminescence (LM) signal recovery (%) after injection of the oxidant was monitored over time by the method in Examples 16 to 19, and time required at each temperature until the LM signal recovery is more than 70% was shown in Table A.

Example 24

In order to describe examples of a method of determining a concentration of uranium (IV) using an oxidant, a microorganism culture media sample expected that uranium (IV) and uranium (VI) coexist with each other therein was sampled, and then a concentration of uranium was determined by a time-resolved laser-induced fluorescence spectroscopy. Desulfovibrio desulfuricans were cultured for two weeks in a culture media including uranium (50 μM), cysteine (1 mM), iron (II) sulfate (2 mM), lactate (10 mM), and carbonate (100 mM). After the sampled culture media was filtered using a 0.45-μm filter under argon atmosphere, the filtered culture media was used as a sample in determining the concentration of uranium. The oxidant composition corresponding to a composition in Example 4 using monopersulfate was added to the detection sample and left at room temperature for 2 hours. Then, four oxidant added samples was sampled 10-mL each. A luminescence enhancer of Example 1 was added to the sampled oxidant added sample, thereby preparing oxidant-luminescence enhancer added samples A.

Among four oxidant-luminescence added samples A, 100, 200, and 300 μL of standard solution (uranium (VI) 2 mM, NaClO$_4$ 0.1 M, pH 2) were added to three samples, respectively, except for one sample to prepare standard solution added sample, and a volume of standard solution added to the each sample was recorded.

Luminescence intensities of uranium (VI) in the oxidant-luminescence enhancer added sample A and each of the standard solution added samples were measured by the method in Example 2, using a time-resolved laser-induced fluorescence spectroscopy. The measured luminescence intensity was shown with respect to a concentration of uranium added in each sample in FIG. 6, wherein the concentration was calculated from a volume of sample, volumes of the added standard solution, and a concentration of the standard solution. A concentration (C(II)) of uranium in the oxidized sample was calculated by the standard addition method.

Four detection samples in which the oxidant is not added were sampled 10-mL each, and the luminescence enhancer of Example 1 was added thereto to prepare luminescence enhancer samples B.

Among four luminescence enhancer added samples B, 100, 200, and 300 μL of standard solution (uranium (VI) 2 mM, NaClO$_4$ 0.1 M, pH 2) were added to three samples, respectively, except for one sample to prepare standard solution added sample, and a volume of standard solution added to the each sample was indicated.

Luminescence intensities of uranium (VI) in the luminescence enhancer added sample B and each of the standard solution added samples were measured by the method in Example 2, using a time-resolved laser-induced fluorescence spectroscopy. The measured luminescence intensity was shown with respect to a concentration of uranium added in each sample in FIG. 6, wherein the concentration was calculated from a volume of a sample, volumes of the added standard solution, and a concentration of the standard solution. A concentration (C(I)) of uranium in the oxidized sample was calculated by the standard addition method.

From the above calculated results, C(II) value was calculated as the concentration of the total uranium in the sample, and a difference between the C(II) value and the C(I) value was calculated as the concentration of uranium (IV).

As set forth above, the method of determining a concentration of uranium according to the present invention may increase accuracy of analysis and rapidly measure the concentration of uranium.

More specifically, according to the present invention, the pre-treatment time of oxidation may be significantly reduced as compared to the method according to the related art by adding the oxidant to the detection target sample, and since only the mixing of the sample and the oxidant is required, it may be advantageous for implementing a simple, miniaturized, and light optical analysis equipment.

Further, since the uranium (IV), the metal ions, and inorganic/organic materials that are included in the detection target sample may be easily oxidized to thereby be converted into compounds interfering less with the luminescence of uranium, the concentration of uranium may be more accurately and simply measured.

What is claimed is:

1. A method of determining a concentration of uranium comprising:
    a) a primary measuring step of adding an oxidant composition to a detection target sample to thereby prepare an oxidant added sample, and then measuring luminescence intensity or luminescence attenuation of uranium (VI) of the oxidant added sample, wherein the oxidant composition includes monopersulfate or ozone;
    b) a secondary measuring step of adding different volumes of standard solution containing uranium (VI) having a predetermined concentration to a plurality of oxidant added samples, respectively, to thereby prepare each standard solution added sample containing the standard solution added thereto, and then measuring luminescence intensity or luminescence attenuation of uranium (VI) contained in each standard solution added sample; and
    c) a calculating step of calculating a concentration of uranium (VI) contained in the detection target sample by a standard addition method based on the primary and secondary measurements.

2. The method of claim 1, wherein step a) includes adding the oxidant composition to the detection target sample, leaving the oxidant added sample at room temperature to 80° C. for 10 minutes to 3 hours to allow uranium (IV), metal ions, and inorganic/organic materials that are included in the detection target sample to be oxidized, and then measuring luminescence intensity or luminescence attenuation of uranium (VI).

3. The method of claim 1, wherein in step a), the oxidant composition further contains one oxidant or a mixture of at least two oxidants selected from hydrogen peroxide, peroxide, percarbonate, dioxide, hypochlorite, persulfate, alkaline peroxide, alkaline earth metal peroxide, urea peroxide, peroxysilicate, peroxyphosphate, ozone, and organic peroxides.

4. The method of claim 3, wherein the oxidant composition is a single oxidant in a liquid state, a granule or powder type solid state, or a gas state of ozone or an oxidant mixture thereof in the same state or different state.

5. The method of claim 4, wherein the oxidant composition is monopersulfate alone, or ozone alone, or a mixture in which one or a mixture of at least two selected from hydrogen peroxide, peroxide, percarbonate, dioxide, hypochlorite, persulfate, alkaline peroxide, alkaline earth metal peroxide, urea peroxide, peroxysilicate, peroxyphosphate, and organic peroxides is mixed with monopersulfate or ozone at a molar ratio of 0.1 to 1.5 based on 1 mol of monopersulfate or ozone.

6. The method of claim 2, wherein in step a), a concentration of the oxidant included in the oxidant added sample is 0.1 to 200 mM.

7. The method of claim 1, wherein step a) includes:
    a1) oxidizing the oxidant added sample in which the oxidant composition is added to the detection target sample;
    a2) preparing an oxidant-luminescence enhancer added sample A in which a luminescence enhancer is added to oxidized oxidant added sample; and a3) measuring luminescence intensity or luminescence attenuation of uranium (VI) of the oxidant-luminescence enhancer added sample A, or a1) oxidizing an oxidant-luminescence enhancer added sample B in which a mixture of the oxidant composition and a luminescence enhancer is added to the detection target sample; and a3) measuring luminescence intensity or luminescence attenuation of uranium (VI) of the oxidant-luminescence enhancer added sample B.

8. The method of claim 7, wherein a volume ratio of the oxidant composition to luminescence enhancer is 1:0.01 to 1:0.5.

9. The method of claim 1, wherein a volume ratio of the detection target sample to the oxidant is 1:0.01 to 1:0.5.

10. The method of claim 7, wherein the luminescence enhancer includes 0.01 to 0.5 mol/L of phosphate, pyrophosphate, polymeric phosphate, or a mixture thereof, and a pH thereof is 0 to 4.

11. The method of claim 1, wherein the luminescence intensity and luminescence attenuation in each step a) and step b) are measured by laser-induced luminescence spectroscopy using a continuous wave laser or a pulse laser.

12. The method of claim 11, wherein the laser-induced luminescence spectroscopy using the pulse laser is a time-resolved laser-induced fluorescence spectroscopy (TRLFS) including a kinetic phosphorescence analysis (KPA) method.

13. The method of claim 1, wherein step c) is a step of calculating the measurement value of the luminescence intensity from the measured results obtained in step a) and step b), calculating measurement value of the luminescence intensity of each of the standard solution added samples in which different volumes of the standard solution are added under the same condition, and making a calibration curve thereof to calculate the concentration of uranium (VI) contained in the detection target sample.

14. The method of claim 1, further comprising a step of determining a concentration of uranium (IV) contained in the detection target sample using a difference between the determined concentration of uranium (VI) and the concentration of uranium (VI) of claim 1 using the detection target sample instead of the oxidant added sample of step a).

* * * * *